(12) United States Patent
Christine et al.

(10) Patent No.: US 6,511,415 B1
(45) Date of Patent: Jan. 28, 2003

(54) DEVICE FOR TRANS-CERVICAL ARTIFICIAL INSEMINATION AND EMBRYO TRANSFER

(75) Inventors: Robert R. Christine, Bethel, MO (US); Ricky A. Schoenbeck, Walworth, WI (US); Donald F. Hladky, Janesville, WI (US)

(73) Assignee: Continental Plastic Corp., Delavan, WI (US)

( * ) Notice: Subject to any disclaimer, the term of this patent is extended or adjusted under 35 U.S.C. 154(b) by 109 days.

(21) Appl. No.: 09/705,489

(22) Filed: Nov. 3, 2000

(51) Int. Cl.⁷ ............................. A61B 17/43; A61D 7/00
(52) U.S. Cl. ......................................................... 600/35
(58) Field of Search ............................. 600/35; 604/515, 604/115, 55, 176, 181, 218, 264, 906, 191

(56) References Cited

U.S. PATENT DOCUMENTS

| | | |
|---|---|---|
| 1,150,214 A | 8/1915 | London |
| 3,467,101 A | 9/1969 | Fogarty et al. |
| 3,805,784 A | 4/1974 | Alter |

(List continued on next page.)

FOREIGN PATENT DOCUMENTS

| | | | |
|---|---|---|---|
| EP | 71538 | 2/1983 | |
| EP | 189702 A1 * | 8/1986 | ............ A61D/7/02 |
| EP | 605406 A2 | 7/1994 | |
| FR | 1525336 | 9/1968 | |
| FR | 0189702 | 12/1985 | |
| FR | 2668054 | 10/1990 | |
| FR | 2701385 A3 * | 8/1994 | ........... A61D/19/02 |
| FR | 2803189 | 6/2001 | |
| GB | 2263642 | 8/1993 | |
| JP | 6-154254 | 6/1994 | |
| WO | WO 97/14365 | 4/1997 | |
| WO | 01/49206 | 7/2001 | |

OTHER PUBLICATIONS

Continental Plastic Corp., electronic brochure entitled "Swine Products", http://www.continentalplastic.com.
"Reproduction Resources Artificial Breeding Equipment and Veterinary Supplies", no date, pp. 1A, 1B, 1–17, 17A.
Polge, C. et al. "Pregnancy following Non–surgical Egg Transfer in Pigs", published in *The Veterinary Record*, Apr. 15, 1968.

(List continued on next page.)

*Primary Examiner*—Max Hindenburg
*Assistant Examiner*—Brian Szmal
(74) *Attorney, Agent, or Firm*—Boyle Fredrickson Newholm Stein & Gratz S.C.

(57) ABSTRACT

The invention relates to an apparatus and a method useful for non-surgical embryo transfer or artifical insemination of mammals. An apparatus for depositing media into the uterus of a mammal includes a conical chamber that has a plurality of perforations and flaps. An exterior spiral formation is configured for traversing or penetrating cervical passageway. A sheath having a frusto-conical rearward end extends axially from an aft end of the conical chamber. A tubular depositing chamber extends axially from the conical chamber to a position beyond a fore end of the conical chamber. Coupled to the rearward end of the depositing chamber is an embryo or semen packaging unit. The tubular depositing chamber has an end that has an aperture to permit the flow of semen out of the depositing chamber and into the uterus. The invention also involves a method for depositing of embryos or semen into a uterus of a mammal by a) inserting a conical chamber having a fore end and an exterior spiral formation into a cervix of a mammal, b) securing the conical chamber with the walls of the cervix, c) projecting a depositing chamber through an interior portion of the conical chamber, d) moving the depositing chamber to an embryo or semen release position for release of embryos or semen in the uterus, and e) securing an embryo or semen packaging unit to the depositing chamber to deposit embryos or semen in the uterus.

26 Claims, 5 Drawing Sheets

U.S. PATENT DOCUMENTS

| | | |
|---|---|---|
| 3,811,443 A | 5/1974 | Dickinson, III et al. |
| 3,910,275 A | 10/1975 | Babey et al. |
| 4,192,294 A | 3/1980 | Vasilevsky et al. |
| 4,261,361 A | 4/1981 | Cassou |
| 4,318,414 A | 3/1982 | Schuster et al. |
| 4,453,936 A | 6/1984 | Cassou |
| 4,474,576 A * | 10/1984 | Gobby ................... 604/115 |
| 4,642,094 A | 2/1987 | North, Jr. et al. |
| 4,832,681 A | 5/1989 | Lenck et al. |
| 4,865,589 A | 9/1989 | Simmet et al. |
| 5,084,004 A | 1/1992 | Ranoux |
| 5,147,315 A | 9/1992 | Weber |
| 5,374,247 A | 12/1994 | Lowery et al. |
| 5,464,409 A | 11/1995 | Mohajer |
| 5,472,419 A | 12/1995 | Bacich |
| 5,496,272 A * | 3/1996 | Chung et al. ............ 604/515 |
| 5,536,243 A | 7/1996 | Jeyendran |
| 5,558,636 A | 9/1996 | Li et al. |
| 5,656,010 A | 8/1997 | Li et al. |
| 5,916,144 A | 6/1999 | Li et al. |
| 5,971,971 A | 10/1999 | Saint-Ramon et al. |
| 6,004,260 A | 12/1999 | Thompson |
| 6,059,716 A * | 5/2000 | Lee et al. ................ 600/35 |

OTHER PUBLICATIONS

Sims, M.M. et. al., "Nonsurgical Embryo Transfer in Swine", published in the *Journal of Animal Science*, vol. 65, Supplement 1, pp. 386 (1987).

Reichenbach, H.D. et al., "Piglets Born after Transcervical Transfer of Embryos Into Recipient Gilts", *Veterinary Record*, 4 pages (1993).

Galvin, J.M. et al., "A Procedure for Successful Nonsurgical Embryo Transfer in Swine", pp. 1280–1289, (1994).

* cited by examiner

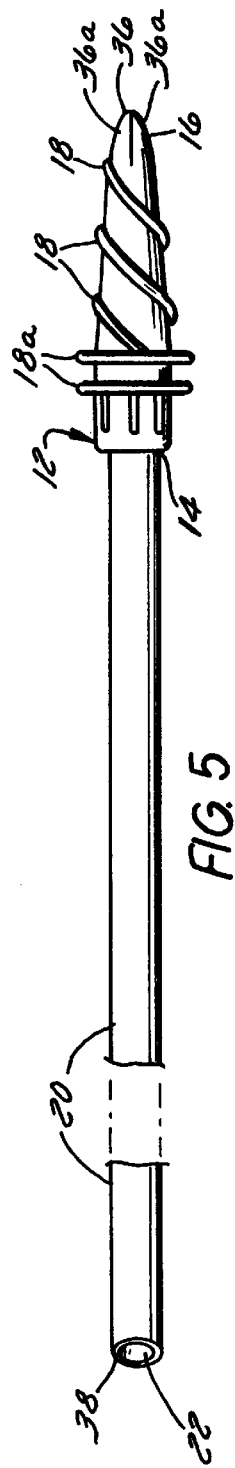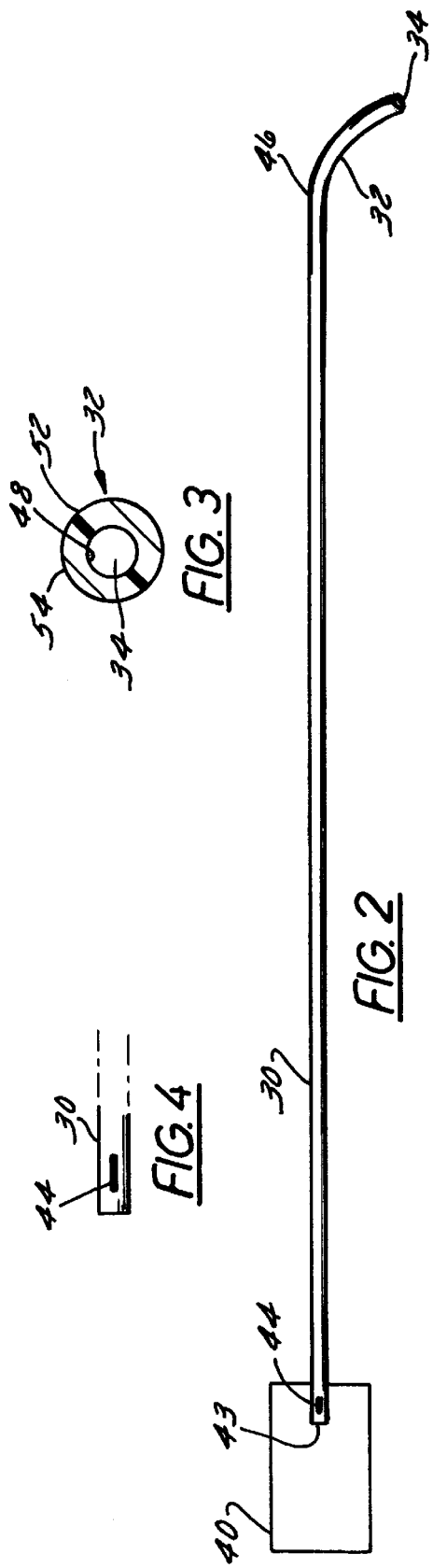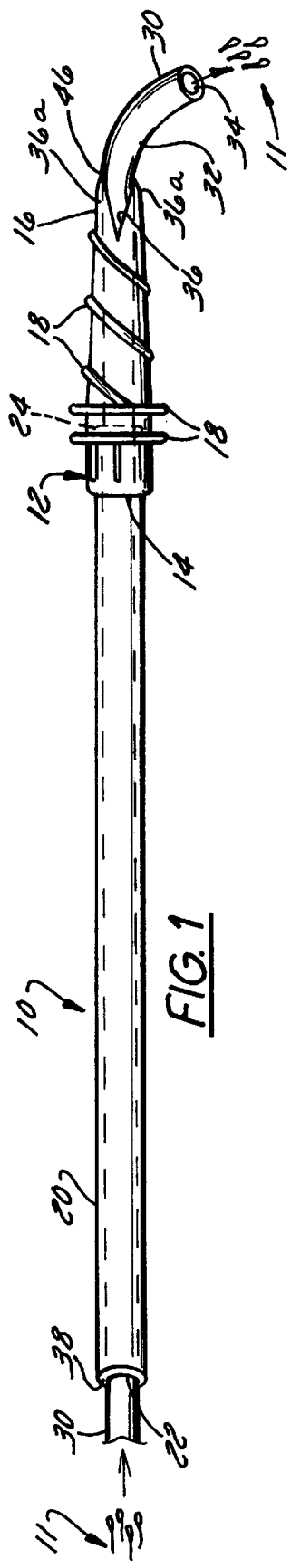

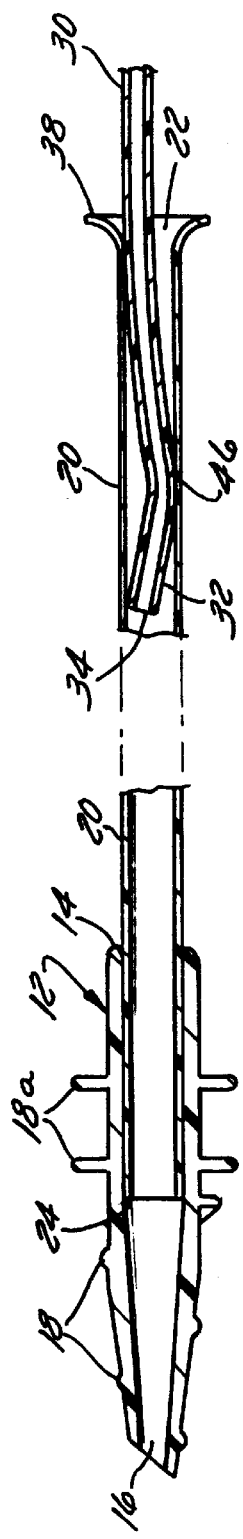
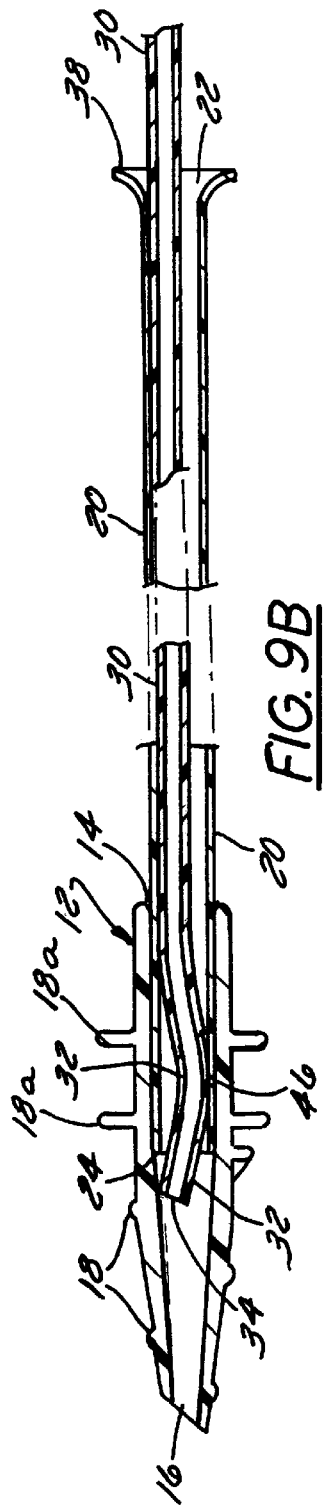
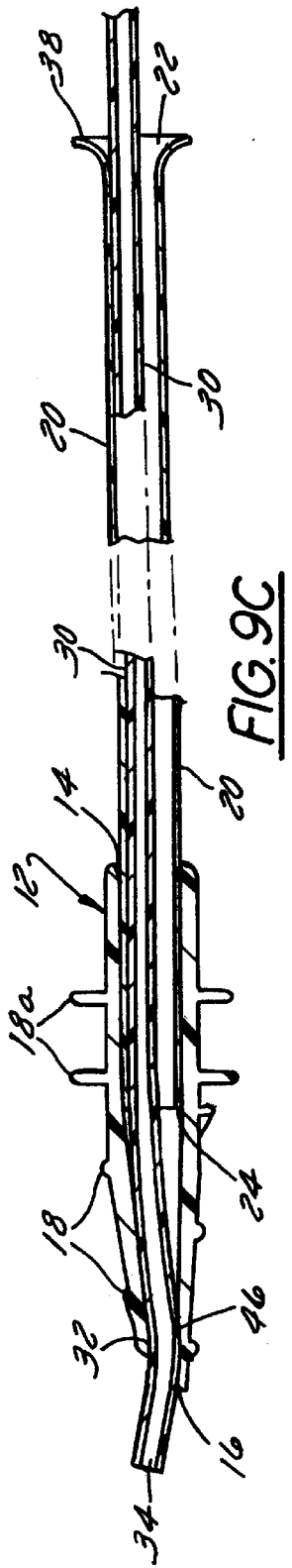

DEVICE FOR TRANS-CERVICAL ARTIFICIAL INSEMINATION AND EMBRYO TRANSFER

BACKGROUND OF THE INVENTION

1. Field of Invention

The present invention relates in general to the field of artificial insemination of mammals. More particularly, the present invention relates to an apparatus and a method useful for non-surgical embryo transfer and artificial insemination of mammals. Specifically, a preferred embodiment of the present invention relates to transfer of fluid medium comprising semen, a fluid medium containing embryos or some medicinal fluid into the uterus of a female mammal such as a sow.

2. Discussion of the Related Art

In recent years, effective application of artificial impregnation including artificial insemination and non-surgical embryo transfer has established a proven method for improving the production of domestic livestock. Generally, such techniques enhanced the ability to selectively breed a single genetically superior male for production traits with a large number of females. Selective breeding of course allows for livestock with improved genetic traits for production. Artificial insemination techniques also decrease the chance of diseases and physical injury that can be associated with the natural breeding process. As a result of these and other advantages, the use of artificial insemination and non-surgical embryo transfer have become a widespread technique in the management of many species of domestic livestock. One of the non-surgical embryo transfer systems described in the prior art, involves inserting a tubular instrument into the cervix of a recipient female, and then depositing 10–12 milliliters of liquid medium containing embryos into and through the instrument, the objective being to deposit the embryos in the uterus. However, other procedures have several drawbacks. First, there is no way to determine whether the instrument has been inserted far enough into the cervix so that its forward end is adjacent to the body of the uterus. As a result, instances where the forward end of the instrument remains lodged within the cervix, the embryos may never reach the uterus to initiate pregnancy, and thus pregnancy rate may be reduced. As a result of the aforementioned problems, the pregnancy rate or liter size in embryo-transfer may be reduced. This results in annual monetary losses due to the cost of maintaining the non-pregnant recipient animals.

Other conventional artificial insemination (AI) techniques in the industry for some species may result in reduced pregnancy rate or litter size because not enough sperm cells were deposited into the uterus. To compensate for this and to maximize pregnancy rate or liter size, larger numbers of sperm cells are introduced than may be necessary if the entire insemination dose was deposited into the uterus. This is also due to the difficulty associated with passing a conventional straight AI device through the cervix of some species. The reason why the passageway of the cervix is difficult to navigate in most mammalian species is that the inside of the cervix has ridged folds of tissue which block straight entry. These folds need to be circumvented to penetrate the cervical passageway and reach the uterine body. Therefore, there is a need for an improved system for affecting the non-surgical transfer of embryos into recipient animals and artificial insemination, particularly those species having a cervix of the type, which is difficult to navigate, such as swine, sheep, and goats.

SUMMARY AND OBJECTIVES OF THE INVENTION

The present invention relates to an apparatus and a method useful for non-surgical impregnation of mammals. Specifically, a preferred embodiment for the present invention relates to transfer of fluid medium comprising semen or a fluid medium containing embryos into the uterus of an animal.

In accordance with one aspect of the invention, an apparatus for depositing semen into a uterus of a mammal includes a conical chamber that has a plurality of perforations. An exterior spiral formation of the chamber is configured for penetrating the spiral cervical passageway, which provides the entrance to the uterine body. A sheath having a frusto-conical rearward end extends axially from an aft end of the conical chamber. A fluid receptacle or semen or embryo packaging unit is coupled to a rearward end of the sheath. A tubular depositing chamber extends axially from the conical chamber to a position beyond a fore end of the conical chamber. The tubular depositing chamber has an end that has an aperture to permit the flow of semen or embryos out of the depositing chamber and into the uterus. An embryo or semen packaging unit is coupled to the rearward end of the depositing chamber.

In accordance with another aspect of the invention, a method of depositing semen or embryos into the uterus of a mammal includes the steps of: a) inserting a conical chamber having a fore end and an exterior spiral formation into cervix of a mammal, b) securing the conical chamber within walls of the cervix, c) projecting a depositing chamber through an interior portion of the conical chamber, d) moving the depositing chamber transcervically to a semen or embryo release position for release of semen or embryos in the uterus, and e) securing a semen or embryo packaging unit to the depositing member to deposit semen or embryos in the uterus.

Another benefit of the present invention is that for artificial insemination directly into the uterus of some species, the insemination time is reduced. Thus, labor costs are minimized. Still another benefit is that the device is inserted while the animal is standing so breeders can safely more quickly delivering the fluid to a multitude of animals and thus be more efficient.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawing accompanying and forming a part of this specification, wherein like reference numerals designate the same elements in the several views, and in which:

FIG. 1 is an elevation view of an apparatus for depositing a medium in a uterus in accordance with the present invention;

FIG. 2 corresponds to FIG. 1 and illustrates a tubular depositing chamber and or embryo or semen packaging unit in accordance with the present invention;

FIG. 3 is an end view of the tubular depositing chamber of FIG. 2 showing a raised curvilinear portion thereof;

FIG. 4 corresponds to FIG. 2 and illustrates a visual marker located on the tubular depositing chamber;

FIG. 5 corresponds to FIG. 1 and illustrates a sheath extending axially from an aft end of a conical chamber;

FIG. 9A corresponds to FIG. 1 with portions broken away to illustrate insertion of the tubular depositing chamber into the sheath;

FIG. 9B corresponds to FIG. 9A and illustrates further insertion of the tubular depositing chamber into the sheath;

FIG. 9C corresponds to FIG. 9A and illustrates complete insertion of the tubular depositing chamber through the sheath;

Figure 6:
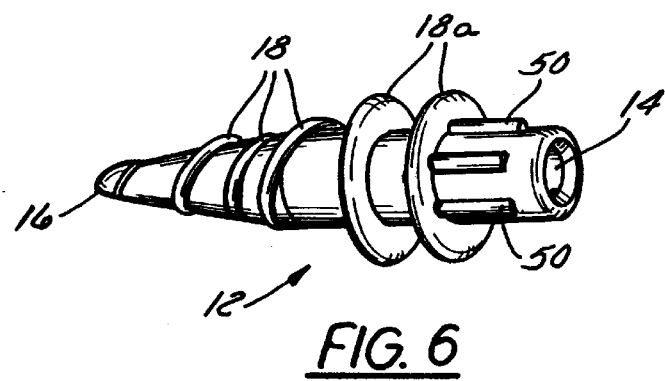
FIG. 6 corresponds to FIG. 1 and shows a perspective view of the conical chamber.

In describing the preferred embodiment of the invention, which is illustrated in the drawings, specific terminology will be resorted to for the sake of clarity. However, it is not intended that the invention be limited to the specific terms so selected and it is to be understood that each specific term includes a technical equivalents which operate in a similar manner to accomplish a similar purpose. For example, the word "connected or terms similar thereto are often used. They are not limited to direct connection but included connection through other elements where such connection is recognized as being equivalent by those skilled in the art.

DETAIL DESCRIPTION OF PREFERRED EMBODIMENTS

The present invention and the various features and advantages details thereof are explained more fully with reference to the non-limiting embodiments described in detail in the following description.

FIG. 1 shows an artificial insemination device or apparatus 10 and its components for depositing of semen or other medium 11 into a uterus of a mammal (not shown). The apparatus 10 comprises a sheath 20, a tubular depositing chamber 30, and a conical chamber 12 to be engaged with one another to transfer semen or other fluid medium from a receptacle or packaging unit 40 (FIG. 2) into the uterus of the mammal. The conical chamber 12 has a fore end 14, and an aft end 16, and an exterior spiral formation 18 configured for penetrating the passageway of a cervix. The fluid 11 could also contain live embryos or some medicine. Two circular sealing rings 18a provide a seal to prevent the fluid from leaking out of the cervix.

FIG. 2 shows the tubular depositing chamber 30 having an arcing end 34 for extending axially from the conical chamber 12 to a position beyond the fore end 16 of the conical chamber 12 as can be seen in FIG. 1. The arcing end 32 includes a flat portion 46 that is configured to abut a distal wall of the uterus to retard further insertion of the depositing chamber 30. As best seen in FIG. 1, the depositing chamber 30 is sized to be slidably inserted from arcing end 32 into the rear end 22 of the sheath 20. The length of tubular depositing chamber 30 is considerably longer than the sheath 20 so that, when fully inserted into the apparatus 10, the depositing chamber 30 projects beyond the forward end 24 of the sheath 20. By way of example, the sheath 20 may have an overall length of 21 inches (in.) and a diameter of 0.25 in. Preferably, the depositing chamber 30 has an overall length of 28 in. and a diameter of 0.09 in. These device dimensions are for an embodiment for a sow. Dimensions for other species will be different.

Figure 10A:
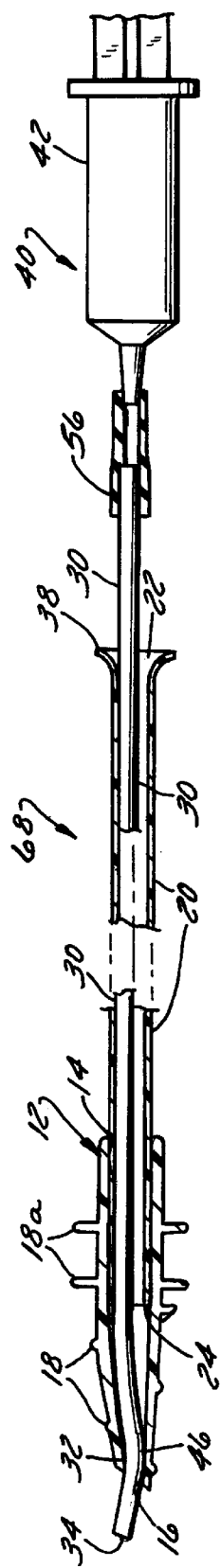
FIG. 10A corresponds to FIG. 1 being broken away to illustrate a first preferred embodiment of a complete artificial insemination device using a syringe.

An adapter 56 is connected to the rearward most end 43 of the depositing chamber 30 as shown in FIG. 10A. The adapter 56 may serve as a handle for the depositing chamber 30 because the adapter 56 may be grasped to manipulate the depositing chamber 30 by rotating it about the latitudinal axis and moving it forward and rearward relative to the sheath 20 inside the cervix.

FIG. 3 shows the arcing end 32 of the depositing chamber 30 has an aperture 34 with a raised curvilinear portion 54, which extends from an inner radius 48 to an outer radius 52. The surface of the portion 54 may be polished to smooth potentially rough edges.

As best viewed in FIG. 4, a visual marker 44 is located on the exterior surface of the depositing chamber 30 to indicate a relative orientation of the arcing end 32 of the depositing chamber 30.

Figure 7:
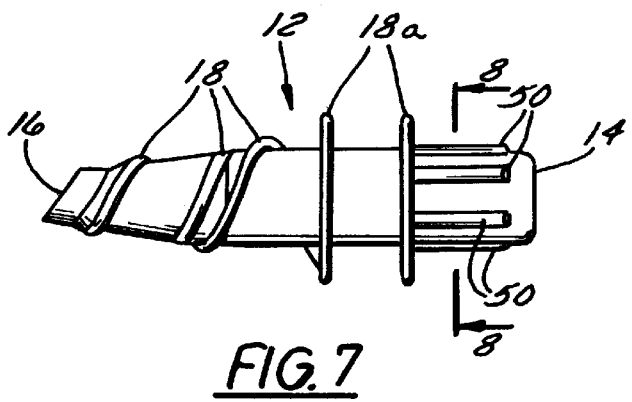
FIG. 7 is a plan view of the conical chamber.
Figure 8:
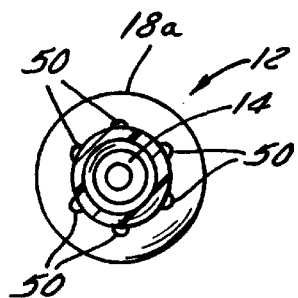
FIG. 8 is a sectional view taken along line 8—8 of FIG. 7.

FIG. 5 shows a portion of the artifical insemination apparatus 10 in which the sheath 20 and the conical chamber 12 are engaged with on another. The conical chamber 12 includes aft and fore ends 14, 16 and the exterior spiral formation 18 configured for penetrating the cervical passageway. The fore end 16 may be truncated as shown in FIG. 7. Alternatively, the aft end 14 of the conical chamber 12 may include a plurality of perforations 36 and flaps 36a extending laterally from the fore end 16 of the conical chamber 12 as best shown in FIG. 5. The 36a flaps, which are of sufficient length to encase the arcing end 32 of the depositing chamber 30 within an interior space of the conical chamber 12. The conical chamber 12 is preferably made of a flexible poly vinyl chloride (PVC) material. The exterior spiral formation 18 allows penetrating easily into the cervix of the mammal.

As best shown in the embodiment of FIG. 7, the conical chamber 12 may have lands 50, which aid during assembly. The lands 50 also provide added friction for gloved hands when pushing inserting the apparatus 10 into the reproductive tract. FIGS. 9A through 9C illustrate the insertion of the tubular depositing chamber 30 into the sheath 20 of the artifical insemination apparatus 10. Referring to FIG. 9A, the arcing end 32 of the tubular depositing chamber is inserted into the rearward end 22 of the sheath 20 and travels through the sheath 20 until it reaches the conical chamber 12 that is connected (preferably by a friction fit or glued) to the forward end 24 of the sheath 20 as shown in FIGS. 9A–C. When the tubular depositing chamber 30 is pushed through the sheath 20, the arcing end 32 of the tubular depositing chamber 30 projects outside of the conical chamber 12 as best shown in FIG. 9C.

Figure 10B:
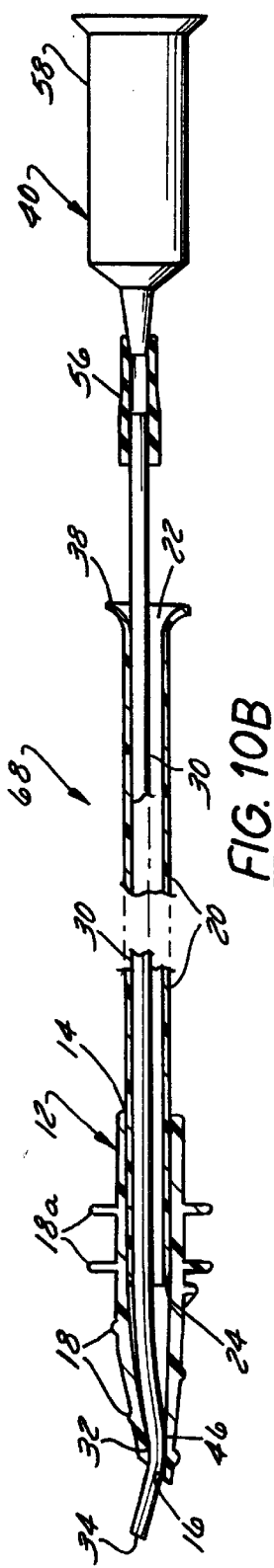
FIG. 10B corresponds to FIG. 1 being broken away to illustrate a second preferred embodiment of complete artificial insemination device using a semen packaging plastic tube.
Figure 10C:
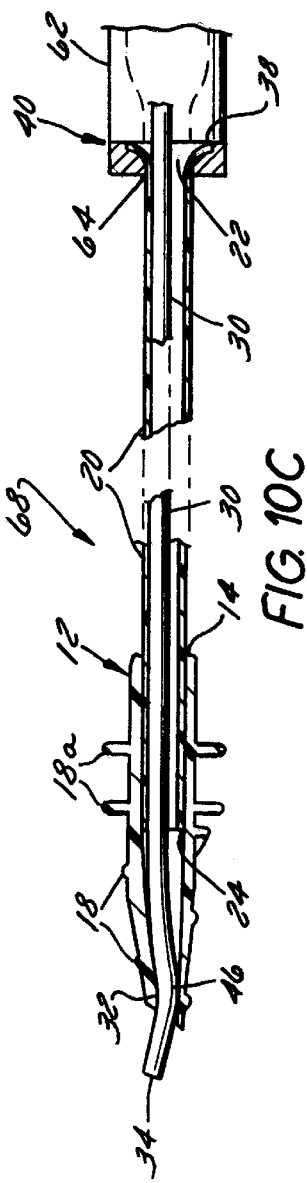
FIG. 10C corresponds to FIG. 1 being broken away to illustrate a third preferred embodiment of a complete artificial insemination device using a plastic bag.

FIGS. 10A through 10C illustrate the operation of the artificial insemination apparatus 10 using different containers or plastic embryo or semen packaging units. Specifically, FIG. 10 shows an apparatus 68 for depositing a medium having the apparatus 10 in communication with a syringe 42. FIG. 10B shows an apparatus 68 having plastic semen packaging tube 58 as a container which can be secured to adapter 56 for transferring semen or other media into the depositing chamber 30. By moving the depositing chamber 30 to the semen release position, the medium is discharged into the uterus.

FIG. 10C shows that the receptacle 40 may be a plastic bag, which has an opening 64 configured to communicate with the rearward end 22 of the depositing chamber 30 to transfer semen or other media to the uterus. The frusto-conical shape 38 of the rear end 22 allows for a tight fitting of the plastic bag 62 to the apparatus 10.

The device 10 is preferably made of plastic materials. The Chamber 12 is made up of a more flexible structure then the sheath 20 or the chamber 30. These materials are better than the stainless-steel of prior art devices as they move efficient and more effective. The plastic devices can be more easily disposed after use or recycled. They are also more inexpensive to produce. Finally, the more flexible parts make the process more comfortable for the animals and as such there is no need to drug the animal.

Figure 11:
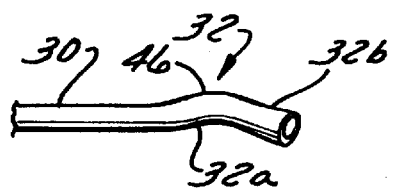
FIG. 11 shows another embodiment of the tubular depositing chamber.

As shown in FIG. 11, another embodiment has an arcing end 32 having a first bend 32a and a second bend 32b. This "double bend" structure can be used to better maneuver the depositing chamber 30 through cervical cavity. This feature also reduces the space, from the left to the right extreme, the depositing chamber 30 would occupy in the cervix. Therefore, the "double bend" arcing end 32 will slip through the spiral conical chamber 12 easier and it should pass through the cervix easier, especially the cervix of gilts, which may be smaller and narrower.

Figure 12:
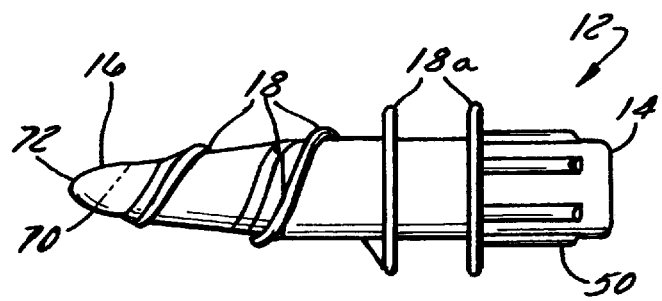
FIG. 12 shows yet another embodiment of the conical chamber.

As shown in FIG. 12, in one embodiment the conical chamber 12 has a completely closed fore end 16 with at least one perforation. The end 16 may be completely sealed for added health and safety reasons such as for keeping the enclosed depositing chamber 30 in a sterile environment until it is ready for use. When ready, the operator will break through the perforated tip 70 and the sterile arcing end of the depositing chamber 30 is then pushed past the perforated end 72 of the chamber 12 and through the cervix into the uterus. In one embodiment having multiple perforations, like the one shown in FIG. 5, the chamber 30 may be used to break through the perforations of the conical chamber 12. However, in this embodiment the perforations do not literally break away.

In Use and Operation

When the device is in use with mammals, it can be used to deposit semen, embryos, medicines or other fluids. The animal need not be sedated and can remain standing during the depositing process unlike during most prior art methods. Specifically, the method of depositing fluid into a mammal includes inserting the forward end of the apparatus 10 (i.e. the conical chamber 12) first into a cervix of a uterus of a mammal. The conical-shaped chamber 12 is manipulated through the cervix by turning connected sheath 20 about an axis and working the apparatus 10 inwardly to the uterus.

This process is made easier by the screw-like, exterior spiral formation 18 of the conical chamber 12. The spiral exterior 18 also helps the operator stimulate the animal on the way to the uterus. Once the conical chamber 12 is in the uterus, it is secured within walls of the cervix by a slight rearward tug of the sheath 20 by the operator. Once secured by the operator, the depositing member or chamber 30 having the arcing end 32 is inserted through the sheath 20. The arcing end 32 is pushed inwardly until it passes through an interior portion of the conical chamber 12. Once the arcing end 32 passes out the depositing chamber 30, it is moved along until the operator experiences substantial resistance to further movement. In one embodiment, the operator can more easily determine the location of this release position by referencing a mark that appears on the shaft of the depositing chamber 30.

Once the operator reaches the fluid release position, a fluid receptacle 40 containing semen or other fluid is then attached to the rear end of depositing member 30. The operator upwardly lifts the attached receptacle 40 to a point where gravity helps the fluid move downwardly into cavity of the depositing chamber 30 and past the conical chamber 12 to deposit the semen or fluid into the uterus.

The individual components described herein need not necessarily be formed in the disclosed shapes, or assembled in the disclosed configuration, but could be provided in virtually any shape, and assembled in virtually any configuration. For example, although the sheath and tubular depositing chamber could be used separately with minor success, combining them increases the ability to transverse the cervical passageway to the uterus Further, although the conical chamber is described herein as a physically separate module, it is apparent that it may be more fully integrated into the sheath. Furthermore, all disclosed features of each disclosed embodiment could be combined with, or substituted for, the disclosed features of every other disclosed embodiment except where such features are mutually exclusive. It is intended that the appended claims cover all such addition, modifications and rearrangements. Expedient embodiments of the present invention are differentiated by the appended sub claims.

What is claimed is:

1. An apparatus for depositing media into a uterus of a mammal, comprising:
   a chamber having a conical fore end, and an aft end, configured for traversing the passageway of a cervix;
   a sheath having a forward end and a rearward end wherein said forward end extends axially from the aft end of the conical chamber, and;
   a tubular depositing chamber having an end extending axially from the conical chamber to a position beyond the fore end of the conical chamber, and wherein the end has:
   (1) an aperture at the fore end,
   (2) an inner radius and an outer radius, and
   (3) a raised curvilinear portion extending from the inner radius to the outer radius.

2. The apparatus of claim 1 wherein the fore end of the conical chamber comprises a plurality of perforations which extend laterally toward the fore end of the conical chamber and are adapted to be of sufficient length to recess within it an arcing end of the depositing chamber.

3. The apparatus of claim 1 wherein the conical chamber is comprised of a flexible polymer.

4. The apparatus of claim 1 further comprising a fluid receptacle attached to the rearward end of the sheath and wherein the rearward end of the sheath further comprises a frusto-conical shape configured to be inserted into the receptacle.

5. The apparatus of claim 1 wherein the depositing chamber has a visual marker situated on and substantially flush with the exterior surface of the depositing chamber to indicate a relative orientation of an arcing end of the depositing chamber.

6. The apparatus of claim 1 further comprising an arcing end of the depositing chamber having a flat portion, the flat portion configured to abut distal wall of the uterus to retard further insertion of the depositing chamber.

7. The apparatus of claim 1 wherein the conical chamber bears at least one land at its aft end.

8. The apparatus of claim 1 wherein the depositing chamber is capable of extending into the uterus at least 17.5 centimeters.

9. The apparatus of claim 1 wherein the chamber having a conical fore end also has flaps permitting extension and retraction of the depositing chamber.

10. An apparatus for artificially impregnating, comprising:
   a conical chamber including an exterior spiral formation configured for traversing a cervical passageway;
   a sheath having a frusto-conical rearward end extending axially from an aft end of the conical chamber;
   a tubular depositing chamber having an arcing end for extending axially from the conical chamber to a position beyond a fore end of the conical chamber;
   the arcing end having a double bend and an aperture to permit the flow of semen out of the depositing chamber and into a uterus; and
   an embryo or semen packaging unit coupled to the depositing chamber at the rearward end of the sheath.

11. The apparatus of claim 10 wherein a plurality of perforations extend laterally from the fore end of the conical chamber within an interior space of the conical chamber.

12. The apparatus of claim 9, wherein the aperture has an inner radius and an outer radius and a smooth surface extending between the inner radius and outer radius.

13. An apparatus for artificially impregnating, comprising:
   a conical chamber including an exterior spiral formation configured for traversing a cervical passageway;
   a sheath having a frusto-conical rearward end extending axially from an aft end of the conical chamber;
   a tubular depositing chamber having an arcing end for extending axially from the conical chamber to a position beyond a fore end of the conical chamber;
   the arcing end having a double bend and an aperture to permit the flow of semen out of the depositing chamber and into a uterus wherein the aperture has an inner radius and an outer radius;
   a raised curvilinear portion extending from the inner radius to the outer radius; and
   an embryo or semen packaging unit coupled to the depositing chamber at the rearward end of the sheath.

14. The apparatus of claim 9 wherein the depositing chamber comprises a visual marker situated on and generally flush with an exterior surface of the depositing chamber.

15. A method for depositing of semen or embryos into a uterus of a mammal comprising the steps of:
   inserting a conical chamber into a cervix of a uterus of a mammal;
   securing the conical chamber having an exterior spiral formation into the cervix of the mammal;
   tugging the device bearing the conical chamber away from the mammal to secure the conical chamber within a wall of a cervical passageway;
   projecting a depositing chamber through an interior portion of the conical chamber;
   moving the depositing chamber to a semen or embryo release position for release of semen or embryos in the uterus;
   securing an embryo or semen packaging unit; and
   depositing embryos or semen in the uterus.

16. The method of claim 15 further comprising the step of moving the conical chamber to a position where there is substantial resistance to further movement.

17. The method of claim 16 further comprising the step of advancing the depositing chamber through the conical chamber to the semen release position for release of the semen in the uterus by breaking through perforations in the conical chamber.

18. The method of claim 17 wherein the step of advancing the depositing chamber further comprises the step of rotating the depositing chamber around an axis to traverse the cervical passageway.

19. The method of claim 18 further comprising the step of orienting the depositing chambers for proper release of the embryos or semen in the uterus.

20. The method of claim 19 wherein the step of orienting the depositing chamber for proper release is accomplished by verifying a projection of an arcing end using a mark on an exterior surface of a rear end of the depositing chamber.

21. A method for depositing of embryos or semen into a uterus comprising the steps of:
   inserting a depositing chamber through an end of a conical chamber;
   recessing an arcing fore end of the depositing chamber in an interior portion of the conical chamber;
   inserting the conical chamber into a cervix;
   pulling the conical chamber slightly rearwardly within the cervix;
   projecting the depositing chamber through the interior portion of the conical chamber;
   advancing the depositing chamber to an embryo or semen release position for release of the embryos or semen in the uterus;
   securing an embryo or semen packaging unit to the depositing chamber; and
   depositing embryos or semen in the uterus.

22. The method of claim 21 further comprising the step of moving the conical chamber to a position where there is substantial resistance to further forward movement.

23. The method of claim 21 further comprising the step of advancing the depositing chamber through the conical chamber to the embryo or semen release position for release of embryos or semen in the uterus.

24. The method of claim 21 wherein the step of advancing the depositing chamber further comprises the step of rotating the depositing chamber about a latitudinal axis to transverse a cervical passageway.

25. The method of claim 24 further comprising the step or orienting the depositing chamber for proper release of the embryos or semen in the uterus.

26. The method of claim 25 wherein the step of orienting the depositing chamber for proper release comprises the step of verifying an end of the depositing chamber is projecting downwardly by properly positioning a mark on an exterior surface of a rear end of the depositing chamber.

\* \* \* \* \*